(12) United States Patent
Redfern et al.

(10) Patent No.: US 6,423,330 B1
(45) Date of Patent: Jul. 23, 2002

(54) PESTICIDAL COMPOSITION AND METHOD

(75) Inventors: Robin Redfern; Allan Nadian; Ian R. Inglis, all of Sand Hutton (GB)

(73) Assignee: The Minister of Agriculture Fisheries and Food in Her Britannic Majesty's Goverment of the United Kingdom of Great Britain and Northern Ireland, London (GB)

( * ) Notice: Subject to any disclaimer, the term of this patent is extended or adjusted under 35 U.S.C. 154(b) by 0 days.

(21) Appl. No.: 09/355,207

(22) PCT Filed: Sep. 11, 1997

(86) PCT No.: PCT/GB97/02445

§ 371 (c)(1),
(2), (4) Date: Jul. 26, 1999

(87) PCT Pub. No.: WO98/10646

PCT Pub. Date: Mar. 19, 1998

(30) Foreign Application Priority Data

Sep. 14, 1996 (GB) ............................................... 9619261

(51) Int. Cl.$^7$ ............................................... A01N 25/28
(52) U.S. Cl. .................. 424/417; 424/405; 424/406; 424/408; 424/43; 424/45; 424/84; 574/743; 574/757; 574/758; 574/760

(58) Field of Search ..................... 424/405, 408–410, 424/417, 418–420, 43, 45, 406, 84

(56) References Cited

U.S. PATENT DOCUMENTS

| | | | | | |
|---|---|---|---|---|---|
| 271,024 | A | * | 1/1883 | Booth | 424/417 |
| 1,502,190 | A | * | 7/1924 | Hezroth | 424/417 |
| 2,585,755 | A | * | 7/1952 | Puopiva | 424/417 |
| 2,957,804 | A | * | 10/1960 | Shuyler | 424/408 |
| 4,178,366 | A | * | 12/1979 | Bedding | 424/93 |
| 4,520,015 | A | * | 5/1985 | Pesche | 424/408 |
| 4,707,355 | A | * | 11/1987 | Wilson | 424/84 |

* cited by examiner

Primary Examiner—Neil S. Levy
(74) Attorney, Agent, or Firm—Nixon & Vanderhye P.C.

(57) ABSTRACT

A mammalian pesticidal composition, and in particular a pesticidal composition for the control of insectivores, in which a pesticidal agent comprising one or more low molecular weight halogenated hydrocarbons, and in particular bromoform, is provided in microencapsulated form, for example, in a coacervated gelatinous base. The resultant microcapsule is preferably provided with a moisture resistant coating which is degradable in a mammalian alimentary system. A method of controlling mammalian pests, in particular insectivores such as moles, using the above composition is also described.

2 Claims, No Drawings

PESTICIDAL COMPOSITION AND METHOD

The invention relates to a mammalian pesticidal composition and method, in particular for the control of small underground dwelling mammals such as moles, shrews and voles.

Small, burrowing, underground-dwelling mammals, and moles in particular, can be a major agricultural pest, particularly to grass cropped areas. Their burrowing activities, or more specifically the earth mounds produced thereby, can result in serious damage to grass cutting equipment and contaminate resultant silage with soil to render it worthless. The creatures can also be pests in the domestic environment, for example in view of the damage done to garden lawns, golf course greens and the like.

The current generally recommended method for mole control is by strychnine poisoning. This technique is an effective and simple one, but it is an inhumane method of killing. Moreover, the high general toxicity of strychnine has led to its misuse against non-target species such as foxes, and necessitated a complex and cumbersome licensing procedure in many parts of the world. Other methods to control such pests, including gassing, trapping, and the use of sonic repellents have been tried, but with generally less efficacy than poison. There is therefore a general desire to develop a practical replacement poison to strychnine for pests of this type.

As a pesticidal agent which is active against mammalian pests, the applicants have found that volatile halogenated hydrocarbons which are generally those of low molecular weight (e.g. 3 or less carbon chain length) are particularly effective, if administered in a lethal dose. Such chemicals are known to have generally both an anaesthetic and in larger doses a toxic effect on some mammals. The use of one such compound, 1,2-dibromoethane, has been described for use as a rodent control agent when applied as a vapour to tunnels.

However, the volatility of these chemicals has rendered them susceptible to rapid dispersal into the environment so that maintaining concentrations at toxic dose levels is difficult. Furthermore, at low levels the chemicals are likely to have a repellent effect on the target. This means that halogenated hydrocarbons are suitably formulated to overcome these problems in order to provide a practical general purpose alternative to strychnine and similar poisons.

According to a first aspect of the invention there is provided the use of a composition comprising as pesticidal agent one or more low volatile halogenated hydrocarbons in microencapsulated form. In particular these compounds are microencapsulated in a gelatinous base.

Suitable gelatinous bases include gelatin, gelatin-gum acacia, gelatin-carrageenan, chitosan-carboxymethyl cellulose and chitosan pectin.

Microcapsules may be formed from these bases by a number of techniques including coacervation, spray drying, spray chilling, suspension separation processes, or centrifugal or other nozzle based extrusion processes.

Suitably the microcapsules comprise the above-described compounds in a coacervated gelatinous base.

The use of microcapsules loaded with the halogenated hydrocarbon overcomes the repellence and dispersal problems associated with the volatility of low molecular weight halogenated hydrocarbons. Additionally, since the first action of the halogenated hydrocarbon is an anaesthetic one, death by exposure to toxic dose levels is preceded by sedation, ataxia and anaesthesia, so that the use of this class of poison can be considered a more humane method of pest control than the use of strychnine and toxins of like action.

Gelatinous bases are generally hydrophilic and may therefore be prone to absorb environmental moisture in use. This can lead to rapid degradation of the microcapsule. The microcapsule is therefore preferably provided with an outer coating layer, which coating layer is of a material which is water resistant to render the microcapsule substantially impervious to moisture but is degradable in a mammalian alimentary system. The outer coating thus provides a moisture barrier to minimize environmental degradation and the leaching of toxins into the groundwater.

It will be understood that such coating must become permeable in the alimentary system if the poison is to take effect. This can conveniently be achieved by applying a coating which degrades in the acidic stomach environment of the target animal, one which degrades in the neutral or alkaline environment of the gut of the target animal, one which is digestible by the enzymes of the gut of the target animal, or one which melts at the body temperature of the target animal.

Suitable coating materials are known in the art. For instance, waxes are available which will melt at body temperature. Other possible coating materials include enteric polymers such as polyvinyl acetate phthalate, cellulose acetate phthalate, anionic copolymers of methacrylic acid and methyl methacrylate, hydroxy propyl methyl cellulose phthalate, and cellulose actetate trimelliate. Another possible coating material comprises a non-degradable coating material such as a polymer which has solid particles which are soluble in either the acid stomach conditions of the alkaline enviroment in the guts distributed throughout. Although this composite coating is complete when the microcapsules are formed, once the capsules come into contact with the conditions prevalent in an animals stomach or gut as appropriate, the solid material dissolves rendering the coating permeable. Suitable solid particles include calcium carbonate, barium carbonate and zinc carbonate. Using this stategy, coating materials such as shellac, fats, waxes, ethylcellulose and its derivatives, methyl methacrylate copolymers, polyethylene, polystyrene and polyvinylidene chloride may be used. A particular coating comprises calcium carbonate embedded in shellac.

Particularly suitable compositions for the pesticidal agent are chloro-, bromo- and iodoalkanes, in particular chloro-, bromo- and iodomethanes, with chloroform, bromoform and iodoform particularly preferred. Small mammals are found to exhibit a particular sensitivity to these agents. The microencapsulated composition produced thereby is thus to some degree targeted to the control of such pests.

Whilst the invention is not limited by any particular theory, it is believed that the toxicity of trihalomethane metabolites may be related to their reducing mechanisms. Free radical intermediates (*$CHBr_2$) were found during aerobic and anaerobic incubation of bromoform with isolated rat hepatocytes. This radical was also detected in vitro incubation of bromoform with liver microsomes from mouse, chicken and turkey. The radical may lead to lipid peroxidation and destruction of cell membranes. The liver metabolism of insectivores appears to be such that they exhibit a particular and unexpected sensitivity to trihalomethanes, and so a pesticidal composition based upon a trihalomethane is thus to some degree targeted to the control of such pests. Thus the use of such compounds in pesticidal baits targeted to these pests forms a further aspect of the invention.

Table 1 below illustrates the significantly enhanced effectiveness of chloroform as an agent against moles, compared with rats and mice. An $LD_{95}$ of chloroform for moles was determined as 200 mg/kg. The table compares this with $LD_{50}$ data for rats and mice. In order to give a reasonable comparison, twice the $LD_{50}$ for rats and mice is compared with the measured $LD_{95}$ for moles. As the table shows, the effectiveness of chloroform on moles is in excess ten times that on rats and mice. It is established that effect of chloroform, bromoform and iodoform tends to follow a similar trend for any given species, so that a similar enhanced effectiveness can be extrapolated for other halomethanes.

Bromoform is particularly preferred and can be used alone as the sole pesticidal agent (save for incidental impurities) since it is less volatile than chloroform, barely soluble in water, and decomposed in air, a process that is speeded up by exposure to sunlight which will limit its tendency to contaminate the environment. In addition, approval for the use of chloroform based products is likely to be more difficult given, for example, its listing as a carcinogen by the EPA.

TABLE 1

Toxicity of chloroform compared from moles, rats and mice

| SPECIES | ORAL $LD_{50}$ (mg/kg) | [2 × (ORAL $LD_{50}$ RAT]/ EFFECTIVE DOSE MOLE |
|---|---|---|
| Mice (Swiss, male) | 1400 | 14 |
| Mice (Swiss, female) | 1550 | 15.5 |
| Rat (Sprague Dawley, male) | 1388 | 13.88 |
| Rat (Sprague Dawley, female) | 1147 | 11.48 |

A microencapsulated composition in accordance with the invention, and in particular one in which bromoform is the principal or sole pesticidal agent, is particularly suited to the control of small, burrowing, underground-dwelling mammals such as moles since it is liable to decomposition in sunlight and therefore less likely to cause harm to surface dwelling small mammals such as hedgehogs, and is less susceptible than strychnine poisons to misuse as a surface poison against foxes and the like.

In a preferred aspect of the invention, the microcapsules containing the pesticidal composition are mixed with gum and added to food attractive to the target animal, such as chopped earthworms, to form a bait. The coating layer providing environmental protection of the gelatinous base remains important in this embodiment, since otherwise the hydrophilic gelatinous base will be degraded by the moist bait which could result in leakage of the pesticidal halogenated hydrocarbon. The resultant tainting of the chopped worms is likely to deter the target animal from taking the bait.

A further aspect of the invention provides for a method of controlling mammalian pests, and in particular a method of controlling small underground dwelling mammals such as moles, shrews and voles, comprising the use as a pesticidal agent of the above-mentioned compositions and baits. In particular the method uses one or more volatile halogenated hydrocarbons microencapsulated in a coacervated gelatinous base and preferably provided with a coating layer, which coating layer is of a material which is water resistant to render the microcapsule substantially impervious to moisture but is degradable in a mammalian alimentary system.

As above described, particularly suitable compositions for the pesticidal agent are chloro-, bromo- and iodoalkanes, in particular the halomethanes, with chloroform, bromoform and iodoform particularly preferred and bromoform most preferred.

A preferred aspect of the method comprises the use as a pesticidal bait of one or more microcapsules containing the pesticidal composition as above described which have first been mixed with gum and added to food selected to be attractive to the target animal, such as chopped earthworms.

A further aspect of the invention provides for a method of controlling small underground dwelling mammals such as moles, shrews and voles, comprising the use as a pesticidal agent of one or more haloalkanes. The method is particularly suited to control of insectivores, particular ground dwelling insectivores such as moles. Chloro, bromo- and iodoalkanes are preferred, and bromoform particularly so.

Details of particular pesticidal compositions and a suitable encapsulation materials and procedure, and a suitable bait incorporating the microencapsulated composition, will now be described by way of example.

EXAMPLE 1

The pH of 140 ml of 1.33% gelatine (Type A with isoelectric point 8-9) solution maintained at 45° C. was adjusted to 6.25 with 10% sodium hydroxide. 25 ml of bromoform, pre warmed to 45° C., was added to the gelatine solution and dispersed with a mechanical stirrer. The droplet size of the bromoform dispersion was adjusted to 300–400 µm and the agitation continued through out the rest of the procedure. 30 ml of 0.5% carrageenanan (Type 1) solution at 45° C. was added to the dispersion dropwise over a 10 minute period. The system was then allowed to cool to 35° C. slowly. 12.5 ml of 10% gelatin solution and 12.5 ml of 10% gum acacia solution, both at 40° C., were added in quick succession to the system. The pH of the system was adjusted to 4.5 with either 10% aqueous acetic acid or 4M hydrochloric acid and allowed to cool to room temperature slowly. Once the system had reached room temperature it was chilled to 4° C. using an ice bath and maintained at the temperature for one hour. 5 ml of 25% aqueous gluteraldehyde solution was added to the chilled system and maintained for a further one hour at 4° C. The ice bath was then removed, the system allowed to warm up to room temperature and maintained for about 18 hours. The microcapsules were then harvested and air dried to give free flowing individual capsules of bromoform.

The dual walled microcapsules produced by this coacervation procedure and having. particle size in the 300 to 450 µm range were very stable when stored under dry conditions. A pay load of more than 80% was obtained.

An example of a method for the production of bait containing capsules in accordance with the invention which is particularly suited to the control of moles will now be described.

The capsules were mixed with paselli and/or farinex gum in the ratio 1:1 gum to capsules. The capsules-plus-gum mixture was then added to chopped earth worms. Earth worms were selected with a view to the identified target animal; it will be readily understood that other bait foodstuffs could be selected for other particular target animals.

When these capsules were incorporated into chopped earth worm bait, the hydrophilic polymer wall of the capsules rapidly swelled in the moist bait which resulted in the leakage of bromoform. The resultant tainting of the chopped earth worms deterred the moles from taking the bait to the detriment of the control strategy. It was, necessary, therefore, to make the capsules impervious to moisture. The dried capsules were over coated with suitable material(s) in a fluidized bed coating machine to provide moisture barrier to the capsules. capsules were over coated with suitable material(s) in a fluidized bed coating machine to provide moisture barrier to the capsules.

Microcapsules produced by the above coacervation procedure were over-coated with moisture resilient materials. Three types of moisture resistant compositions were used: a combination of shellac and relatively high melting wax; a slurry of micronized calcium carbonate in shellac solution; and an enteric polymer such as polyvinyl acetate phthalate, which can be used either on its own or in combination with a high melting point wax. The acidic nature of the moles stomach eroded the calcium carbonate and made the capsules permeable to moisture. The fat or the wax coatings were either digested by the enzymes in the gut of the mole or they melted at the body temperature of the animal, the two mechanisms rendering the capsules susceptible to moisture. The enetric coating disintegrated in the alkaline conditions of the mole gut and made the capsules permeable to moisture.

The worms were cut into segments for two reasons. First, moles do not try to cache chopped worms and hence the bait is not carried away from the original site. Second, moles do not attempt to clean the outsides of small segments of worms: instead the segments are eaten whole thus ensuring maximum uptake of capsules. The amount of bait should be approximately the maximum a mole will consume at one meal. The bait was mixed as follows 1 g gum: 1 g capsules on 16 g worms.

What is claimed is:

1. A pesticidal agent suitable for inclusion in a bait for controlling moles consisting essentially of solid microcapsules formed of a gelatinous base and filled with one or more volatile halogenated hydrocarbons selected chloro-, bromo- and iodo $C_1$–$C_3$ alkanes in which the gelatinous base encapsulates the hydrocarbon sufficiently to suppress escape of the hydrocarbon therefrom, each microcapsule having a water resistant outer coating layer thereon to render it substantially impervious to moisture, the coating also being degradable in the alimentary system of a mole to enable the pesticidal agent to release the halogenated hydrocarbon in a dosage lethal to moles.

2. A pesticidal agent for controlling moles comprising:

(1) solid microcapsules formed of a gelatinous base and filled with one or more volatile halogenated hydrocarbons selected chloro-, bromo- and iodo $C_1$–$C_3$ alkanes in which the gelatinous base encapsulates the hydrocarbon sufficiently to suppress escape of the hydrocarbon therefrom, each microcapsule having a water resistant outer coating layer thereon to render it substantially impervious to moisture, the coating also being degradable in the alimentary system of a mole to enable the pesticidal agent to release the halogenated hydrocarbon in a dosage lethal to moles, (2) a coating of gum over the outer surface of the solid microcapsules, and (3) a food attractive to moles.

* * * * *